United States Patent [19]

Oliver et al.

[11] Patent Number: 6,054,488
[45] Date of Patent: Apr. 25, 2000

[54] MEDICINAL AEROSOL FORMULATIONS OF FORMOTEROL

[75] Inventors: Martin J. Oliver; Simon G. Paling; Philip A. Jinks; Sukhbinder K. Jaiswal, all of Leicester, United Kingdom

[73] Assignee: 3M Innovative Properties Company, St. Paul, Minn.

[21] Appl. No.: 09/088,871

[22] Filed: Jun. 2, 1998

Related U.S. Application Data

[63] Continuation of application No. PCT/US97/09471, Jun. 2, 1997
[60] Provisional application No. 60/048,233, Jun. 2, 1997.

[30] Foreign Application Priority Data

Jun. 11, 1996 [GB] United Kingdom .................... 9612297

[51] Int. Cl.$^7$ ............................................... A61K 31/135
[52] U.S. Cl. ........................................................ 514/646
[58] Field of Search ............................................. 514/646

[56] References Cited

U.S. PATENT DOCUMENTS

| | | | |
|---|---|---|---|
| 2,868,691 | 1/1959 | Porush et al. | 167/54 |
| 3,014,844 | 12/1961 | Thiel et al. | 167/82 |
| 5,182,097 | 1/1993 | Byron et al. | |
| 5,225,183 | 7/1993 | Purewal et al. | |
| 5,439,670 | 8/1995 | Purewal et al. | |
| 5,605,674 | 2/1997 | Purewal et al. | |
| 5,653,962 | 8/1997 | Akehurst et al. | |
| 5,658,549 | 8/1997 | Akehurst et al. | |
| 5,674,471 | 10/1997 | Akehurst et al. | |
| 5,674,473 | 10/1997 | Purewal et al. | |
| 5,676,929 | 10/1997 | Akehurst et al. | |
| 5,681,545 | 10/1997 | Purewal et al. | |
| 5,683,677 | 11/1997 | Purewal et al. | |
| 5,695,743 | 12/1997 | Purewal et al. | |
| 5,720,940 | 2/1998 | Purewal et al. | |
| 5,736,124 | 4/1998 | Akehurst et al. | |
| 5,744,123 | 4/1998 | Akehurst et al. | |
| 5,766,573 | 6/1998 | Purewal et al. | |
| 5,776,434 | 7/1998 | Purewal et al. | |

FOREIGN PATENT DOCUMENTS

| | | |
|---|---|---|
| 209547B1 | 1/1987 | European Pat. Off. . |
| 372777B1 | 6/1990 | European Pat. Off. . |
| 384371B1 | 8/1990 | European Pat. Off. . |
| 504112A2 | 9/1992 | European Pat. Off. . |
| 617610B1 | 10/1994 | European Pat. Off. . |
| 656207A1 | 6/1995 | European Pat. Off. . |
| 2288978 | 11/1995 | United Kingdom . |
| 91/04011 | 4/1991 | WIPO . |
| 91/11173 | 8/1991 | WIPO . |
| 91/11495 | 8/1991 | WIPO . |
| 91/11496 | 8/1991 | WIPO . |
| 92/22286 | 12/1992 | WIPO . |
| 92/22287 | 12/1992 | WIPO . |
| 93/11745 | 6/1993 | WIPO . |
| 93/11747 | 6/1993 | WIPO . |
| WO 9311747 | 6/1993 | WIPO . |
| 94/21228 | 9/1994 | WIPO . |
| 94/21229 | 9/1994 | WIPO . |
| 96/18384 | 6/1996 | WIPO . |
| 96/19968 | 7/1996 | WIPO . |
| 97/47286 | 12/1997 | WIPO . |

OTHER PUBLICATIONS

Kontny, M.J.; Destefano, G.; Jager, P.D.; McNamara, D.P.; Turi, J.S.; and Van Campen, L. "Issues Surrounding MDI Formulation Development with Non–CFC Propellants", *Journal of Aerosol Medicine*, vol. 4, No. 3, 1991, pp. 181–187, Mary Ann Liebert, Inc., Publishers.

Tansey, Ian P. "The challenges in the development of metered dose inhalation aerosols using ozon–friendly propellants", *Spray Technology & Marketing for Jul. 1994*, pp. 26–29.

Sharpe, R., "Development of a metered dose inhaler using one of the new HFA Propellants", *Aerosol and SprayReport*, vol. 35, No. 3/96, pp. 127–129.

Dalby, Richard N.; Byron, Peter R.; Shepherd, H.R.; and Papadopoulos, Elaine, "CFC Propellant Substitution: P—134a as a Potential Replacement for P—12 in MDIs", *Pharmaceutical Technology*, Mar. 1990, pp.—26–33.

Jinks, P.A., "A Rapid Technique for Characterisation of the Suspension Dynamics of Metered Dose Inhaler Formulations", Proceedings of Drug Delivery to the Lung, VI P. 10–13 (Dec. 1995) printed by The Aerosol Society.

Phillips, Elaine M., "Crystal Growth—Formulation Dependence and Early Detection", *Journal of Biopharmaceutical Sciences*, 3(½) 1992, pp.—11–18.

Smith, Ian J. "The Challenge of Reformulation", *Journal of Aerosol Medicine*, vol. 8, Supplement 1, 1995, Mary Ann Liebert, Inc., Publishers, pp.—s–19—s–27.

*Primary Examiner*—Raymond Henley, III
*Attorney, Agent, or Firm*—Ted K. Ringsred; Robert W. Sprague; Gary L. Griswold

[57] ABSTRACT

A pharmaceutical suspension formulation suitable for aerosol administration having from 0.0025 to 0.1% w/w of micronized Formoterol, or an acid addition salt thereof, from 0.1 to 5.0% w/w ethanol, HFA 134a, HFA 227 or a mixture of HFA 227 and HFA 134a, and optionally a surfactant other than a monoacetylated or diacetylated monoglyceride, the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug.

19 Claims, No Drawings

MEDICINAL AEROSOL FORMULATIONS OF FORMOTEROL

This application claims the benefit of the filing date of U.S. provisional application No. 60/048,233, filed Jun. 2, 1997; also and, is a continuation of international application PCT/US97/09471, filed Jun. 2, 1997, which claims priority to Great Britain application GB 96.12297, filed Jun. 11, 1996.

FIELD OF THE INVENTION

This invention relates to medicinal aerosol formulations and in particular to aerosol formulations containing Formoterol Fumarate which are suitable for administration to the respiratory system of a patient.

BACKGROUND

Most pharmaceutical suspension aerosol formulations currently use a mixture of liquid chlorofluorocarbons as the propellant. Fluorotrichloromethane, dichlorodifluoromethane and dichlorotetrafluoroethane are the most commonly used propellants in aerosol formulations for administration by inhalation.

Chlorofluorocarbons (CFCs), however, have been implicated in the destruction of the ozone layer and their production is being phased out. Hydrofluorocarbon 134a (HFA 134a, 1,1,1,2-tetrafluoroethane) and hydrofluorocarbon 227 (HFA 227, 1,1,1,2,3,3,3-heptafluoropropane) are viewed as being more ozone friendly than many chlorofluorocarbon propellants; furthermore, they have low toxicity and vapor pressures suitable for use in aerosols.

W091/11495 and W091/11496 disclose pharmaceutical suspension aerosol formulations comprising a medicinal agent, a surfactant, and a propellant mixture containing 1,1,1,2,3,3,3-heptafluoropropane and one or more additional components, e.g. pentane, butane, propellant 134a, propellant 11, propellant 125, or propellant 152a.

EP 0384371 discloses solution aerosols in which 1,1,1,2,3,3,3-heptafluoropropane or its mixture with propane, butane, isobutane, dimethyl ether, or 1,1, difluoroethane serves as the propellant. The application does not, however, disclose suspension aerosols or pharmaceutical aerosol formulations.

EP 0372777 discloses, inter alia, examples of aerosol formulations comprising a medicament, 1,1,1,2-tetrafluoroethane, a surface active agent, and at least one compound having higher polarity than 1,1,1,2-tetrafluoroethane.

U.S. Pat. No. 2,868,691 discloses aerosol formulations comprising a medicament, a halogenated lower alkane propellant, and a co-solvent which assists in dissolving the medicament in the propellant. The chemical formula for the propellant given in column 2, lines 6 to 16, generically embraces HFA 134a and HFA 227. Examples of co-solvents disclosed include ethanol and diethyl ether.

U.S. Pat. No. 3,014,844 discloses aerosol formulations comprising a micronised medicament, a halogenated lower alkane propellant and a surface-active agent to assist in the suspension of the medicament in the propellant. The chemical formula for the propellant given in column 4, lines 17 to 28, generically embraces HFA 134a and HFA 227.

W091/04011 discloses aerosol compositions having HFA 134a as the propellant and comprising a medicament coated with a non-perfluorinated surface active dispersing agent.

W093/11747 discloses a pharmaceutical suspension formulation suitable for aerosol administration, consisting essentially of a therapeutically effective amount of a drug and a propellant selected from the group consisting of HFA 134a, HFA 227, and a mixture thereof, the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug. The application specifically discloses formulations of Formoterol Fumarate in HFA 134a, HFA 227 and 1:1 mixtures of HFA 134a and HFA 227. The formulations do not contain surfactants or ethanol. It is stated that mixtures of HFA 134a and HFA 227 may be adjusted for density matching with the drug.

W093/11745 discloses pharmaceutical aerosol formulations, substantially free of surfactant containing fluorocarbon or hydrogen-containing chlorofluorocarbon propellants and up to 5% of a polar co-solvent. Preferred propellants are HFA 134a and HFA 227 which are preferably used alone. The preferred polar co-solvent is ethanol and it is stated that in general only small quantities e.g. 0.05 to 3.0% w/w of polar co-solvent are required to improve the dispersion and the use of quantities in excess of 5% w/w may disadvantageously tend to dissolve the medicament.

EP-A-0504112 discloses a pharmaceutical composition for aerosol use containing:

(a) a liquefied propellant gas or propellant gas mixture with a vapor pressure exceeding 1 bar but less than 6 bar (20° C.) from the unsubstituted or partially to completely fluorinated hydrocarbon group;

(b) a non-ionic tensile of the monoacetylated or diacetylated monoglyceride group;

(c) a pharmaceutical active substance or combination of active substances, and, if necessary, (d) other common pharmaceutical accessory substances suitable for aerosol formulations.

It is stated the basic purpose of that invention was to find a special accessory suspending substance for active substances in aerosol formulations, which dissolves better in liquefied "alternative" propellant gases than the accessory suspending substances hitherto recognized and used. Surprisingly, it was discovered, in solving this problem, that non-ionic tensides of the monoacetylated or diacetylated monoglyceride group are very soluble in the "alternative" propellant gases mentioned, particularly in heptafluoropropane (HFA 227), are beneficial to the production of homogenous suspensions, and also have outstanding metering valve lubrication properties. Some of the examples of EP-A-0504112 disclose formulations comprising Formoterol Fumarate.

Formoterol Fumarate is a long acting $B_2$ agonist which has been developed for delivery to the respiratory system by a metered dose inhaler (MDI). The drug is highly potent and its dosage is considerably less than many other drugs which have been administered by MDIs. Thus, the concentration of Formoterol Fumarate in aerosol formulations is very low and this factor, together with other properties of the drug have led to problems in manufacturing and formulating a composition which is stable and provides good dosage reproducibility when administered by MDIS.

Aerosol formulations consisting of propellant, e.g. HFA 134a, HFA 227 and mixtures thereof, and Formoterol Fumarate without additional excipient sometimes encounter problems such as caking on manufacturing equipment, high deposition in the vial or valve of inhalers and valve sticking.

Aerosol compositions consisting of Formoterol Fumarate, HFA 134a and ethanol have proved to be extremely sensitive to ethanol concentration. An ethanol concentration of 3.5% w/w may cause unacceptable crystal growth.

SUMMARY OF THE INVENTION

It is an object of the present invention to provide stable aerosol compositions containing Formoterol Fumarate.

According to one aspect of the present invention there is provided a pharmaceutical suspension formulation suitable for aerosol administration, consisting essentially of:

(a) from 0.0025 to 0.1% w/w of micronized Formoterol, or an acid addition salt thereof and (b) from 0.1 to 5.0% w/w ethanol, (c) HFA 134a, HFA 227 or a mixture of HFA 227 and HFA 134a and optionally (d) a surfactant other than a monoacetylated or diacetylated monoglyceride, the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug.

According to a second aspect of the invention, there is provided a pharmaceutical suspension formulation suitable for aerosol administration, consisting essentially of:

(a) from 0.0025 to 0.1% w/w of micronised Formoterol, or an acid addition salt thereof, (b) from 0.1 to 5.0% w/w ethanol, (c) a propellant consisting of HFA 134a, HFA 227 or a mixture of HFA 227 and HFA 134a, (d) a micronised bulking agent in a weight ratio in the range from 1:3 to 1:100 of Formoterol: bulking agent, and optionally (e) a surfactant, the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug.

DETAILED DESCRIPTION

It has been found that improved aerosol formulations comprising Formoterol Fumarate may be obtained by utilizing low concentrations of ethanol. The combination of HFA 134a and HFA 227 in a weight ratio of HFA 134a: 227 from 50:50 to 30:70 provides a propellant system in which the drug has good stability. The preferred ratio is about 37.5:62.5.

Alternatively, stable formulations may be obtained by the incorporation of a micronised bulking agent which will sediment in the propellant e.g. lactose, DL-Alanine, ascorbic acid, glucose and D+ trehalose dehydrate. The micronised bulking agent may prevent the drug from creaming by co-flocculating with the drug, the resultant floes are denser than the propellant and will sediment leaving no creamed layer upon prolonged standing. The weight ratio of drug to bulking agent is in the range 1:3 to 1:100, generally from 1:3 to 1:20. If the concentration of bulking agent is too low, not all of the drug will sediment and a small amount will cream. If the concentration is too high, the formulation may flocculate and either sediment or cream too quickly for acceptable use as an aerosol formulation.

The presence of ethanol assists in the stability, the general performance and in the manufacturing of the formulation. Preferably ethanol is present at a concentration in the range 1.5 to 3.5%, more preferably about 2.5% w/w in formulations which do not employ bulking agent. In formulations containing bulking agent ethanol is generally present at about 1% w/w as this has been sufficient to provide the above benefits.

The composition of the invention may comprise a surfactant. Low levels of surfactant, often below the levels normally used for the purposes of stabilizing suspensions and valve lubrication in aerosol formulations, have been shown surprisingly to provide a flocculant effect to produce stable floccular dispersions. Levels of oleic acid of 0.002 to 0.01% w/w have provided useful properties, a preferred concentration is about 0.005% w/w. Other surfactants and/or larger levels of surfactant may be used.

The concentration of Formoterol Fumarate depends upon the dose required and the metering volume of the valve. Concentrations of 0.01% w/w and 0.02% w/w have proved to be suitable, using a 50 microlitre valve.

It is conventional practice when preparing aerosol formulations to mix the drug with the highest boiling point material and thereafter mix with the propellant. However, when making the formulations of the present invention it is important to ensure the Formoterol Fumarate does not come into contact with high concentrations e.g. above 10% w/w, of ethanol since the drug would dissolve leading to instability and crystal growth problems in the final formulation. Preferably the maximum concentration of ethanol during formulation is less than 5%. A suitable method for manufacturing formulations on a pilot scale is as follows.

The ingredients arc divided into those for making the concentrate and those for including in the bulk.

The concentrate contains the drug and optional bulking agent, sufficient propellant to disperse them and ethanol, preferably not in excess of 5 percent of the weight of the concentrate, more preferably about 2.5% The bulk contains most of the propellant, the balance of the ethanol and optional surfactant.

The bulk ingredients are fed into a batching vessel, which is either chilled to approximately −55° C. for the purposes of cold filling, or is pressure resistant for pressure filling.

In a glove box purged with dried air, a small quantity of propellant is added to a prechilled stainless steel concentrate vessel. Prechilled ethanol is added. A homogenizer is inserted into the concentrate vessel. Preweighed drug and optional bulking agent are added slowly to disperse. This forms the concentrate.

After dispersing, the concentrate is added to the bulk propellant in the batching vessel and mixed continuously until all of the formulation has been dispensed.

The bulk formulation is either dispensed chilled into open aluminum cans, which are immediately sealed with a metering valve on each can, or pressure filled into cans which have previously been sealed with metering valves.

The invention will be illustrated by the following Examples.

In the Examples, unless otherwise stated, the following preparation technique was employed.

The formulations were prepared in the laboratory by dispensing the active and if required the bulking agent into a preweighed vial. This was then sealed with a non-metering valve and the premixed ethanol/propellant and optional surfactant injected into the vial. The vial was then subjected to ultrasonic energy to disperse the solid particles.

EXAMPLES 1 to 5

The following formulations were prepared (FF denotes Formoterol Fumarate):

|  | Example 1 % w/w | Example 2 % w/w | Example 3 % w/w | Example 4 % w/w | Example 5 % w/w |
|---|---|---|---|---|---|
| FF | 0.010 | 0.010 | 0.010 | 0.010 | 0.010 |
| Ethanol | 2.500 | 2.500 | 2.500 | 2.500 | 2.500 |
| HFA 227 | 48.745 | 65.806 | 63.368 | 60.931 | 56.057 |
| HFA 134a | 48.745 | 31.684 | 34.121 | 36.559 | 41.433 |
|  | 100.00 | 100.00 | 100.00 | 100.00 | 100.00 |

Measured Density of Formulations (g/ml)

|  | Temperature (Deg. C.) | | | Propellant radio (w/w) |
|---|---|---|---|---|
| Example | 20 | 25 | 30 | HFA 227:HFA 134a |
| 1 | 1.285 | 1.266 | 1.247 | 50.0:50.0 |
| 5 | 1.298 | 1.279 | 1.259 | 57.5:42.5 |
| 4 | 1.307 | 1.288 | 1.269 | 62.5:37.5 |
| 3 | 1.312 | 1.293 | 1.272 | 65.0:35 |
| 2 | 1.317 | 1.298 | 1.277 | 67.5:32.5 |

The above formulations were designed such that the density of the liquid component was fairly close to that of Formoterol Fumarate.

These formulations had the following creaming and sedimenting characteristics at 20° C.

Formulation 1 just sedimented. Formulation 2 creamed. Formulation 4 gradually creamed at 20° C. but gradually settled at 30° C. when observed over a 12 hour period.

Each formulation was tested for uniformity of drug dosing, after storage periods of up to 24 hours at ambient temperature in order to simulate patient use. Formulation 4 gave the most consistent performance in these tests.

Formulations containing oleic acid

The following formulations were prepared:

|  | Example 4 % w/w | Example 6 % w/w | Example 7 % w/w | Example 8 % w/w | Example 9 % w/w |
|---|---|---|---|---|---|
| FF | 0.010 | 0.010 | 0.010 | 0.010 | 0.010 |
| Oleic Acid | 0 | 0.0001 | 0.0003 | 0.0005 | 0.001 |
| Ethanol | 2.500 | 2.500 | 2.2500 | 2.500 | 2.500 |
| HA 227 | 60.931 | 60.931 | 60.931 | 60.931 | 60.931 |
| HFA 134a | 36.559 | 36.559 | 36.559 | 36.559 | 36.558 |
|  | 100.000 | 100.000 | 100.000 | 100.000 | 100.000 |

|  | Example 10 % w/w | Example 11 % w/w | Example 12 % w/w | Example 13 % w/w | Example 14 % w/w | Example 15 % w/w |
|---|---|---|---|---|---|---|
| FF | 0.010 | 0.010 | 0.010 | 0.010 | 0.010 | 0.010 |
| Oleic Acid | 0.002 | 0.003 | 0.004 | 0.005 | 0.007 | 0.009 |
| Ethanol | 2.500 | 2.500 | 2.500 | 2.500 | 2.500 | 2.500 |
| HFA 227 | 60.930 | 60.929 | 60.929 | 60.928 | 60.927 | 60.926 |
| HFA 134a | 36.558 | 36.558 | 36.557 | 36.557 | 36.556 | 36.555 |
|  | 100.000 | 100.000 | 100.000 | 100.000 | 100.000 | 100.000 |

The formulations had the following characteristics:

Low levels of oleic acid have been shown surprisingly to impart a flocculant effect to produce stable floccular dispersions, which may allow less migration of drug to and from the metering chamber of the valve than surfactant-free formulations. This is because the floc size of the formulations is larger. visual differences were apparent for surfactant levels when comparing 0% oleic acid with 0.005 to 0.009% oleic acid. Formulations containing 0.0001 to 0.001% oleic acid showed no difference from the 0% oleic acid formulation, when examined either visually or by using an optical measuring technique such as that described in the Proceedings of Drug Delivery to the Lung VI p. 10–13 (December 1995) printed by The Aerosol Society. Examples 9 to 13 having 0.001% to 0.005% in steps of 0.001% oleic acid showed increasing effect, which was measurable at the 0.002% level in Example 10.

EXAMPLES 16 to 22

Use of Bulking Agent

In order to study the suspension characteristics of lactose bulked formulations a range of units was prepared. The ratio of Formoterol Fumarate (FF) to lactose (L) was varied between 1:1 and 1:7 and suspended in a mixture of Ethanol:HFA 227, 1:99 using the following formulations:

|  | Example | | | | | | |
| --- | --- | --- | --- | --- | --- | --- | --- |
|  | 16 | 17 | 18 | 19 | 20 | 21 | 22 |
|  | | | | FF:L | | | |
|  | 1:1 % w/w | 1:2 % w/w | 1:3 % w/w | 1:4 % w/w | 1:5 % w/w | 1:6 % w/w | 1:7 % w/w |
| FF | 0.009 | 0.009 | 0.009 | 0.009 | 0.009 | 0.009 | 0.009 |
| Lactose | 0.009 | 0.019 | 0.028 | 0.038 | 0.047 | 0.056 | 0.066 |

All formulations were made up to 100% with Ethanol:HFA 227 at 1:99 by weight.

The following method was used to prepare the formulations:

i) The propellant mix was made up in a 500 ml can by first weighing out 1 g of ethanol and crimping on a 1 inch continuous valve. 99 g of HFA 227 was then injected into the can through the valve.

ii) The Formoterol Fumarate and the lactose were weighed directly into transparent vials.

iii) A non-metering valve was crimped onto each vial.

iv) The vials were filled with the prescribed amount of propellant mix from the 500 ml can using a transfer button, to transfer some propellant mix via the valves of the can and the vial.

v) The vials were placed in an ultrasonic bath for four minutes to homogenize the formulation.

Result

The resulting suspensions were examined visually.

They were found to form fairly coarse flocs, which tended to sediment. The sedimentation rate increased with lactose concentration. For weight ratios of greater lactose content than 1:7, more rapid sedimentation would occur which could lead to a general loss of dosing reproducibility.

Formulations 19 and 22 were tested for uniformity of drug dosing, after storage periods up to 24 hours, in order to simulate patient use. Formulation 22 gave the most consistent performance in these tests.

EXAMPLES 23 and 24

Effect of Different Ethanol Concentration with Bulking Agent

The formulation of Example 22 (1% ethanol) was compared with formulations containing 2 and 3% ethanol. The following formulations were prepared:

|  | Example | | |
| --- | --- | --- | --- |
|  | 22 | 23 | 24 |
|  | Percentage of ethanol | | |
|  | 1% | 2% | 3% |
| % w/w | | | |
| FF | 0.009 | 0.009 | 0.0009 |
| Lactose | 0.066 | 0.066 | 0.066 |
| Ethanol | 1.000 | 2.000 | 3.000 |
| HFA 227 | 98.925 | 97.925 | 96.924 |
|  | 100.000 | 100.000 | 100.000 |

Results

No visual difference was observed in the size of the flocs or the floc settling rate obtained with the three concentrations of ethanol used. Thus the beneficial effects of adding ethanol were realized by including the minimum amount (i.e. 1% ethanol).

EXAMPLE 25

Use of Different Bulking Agents with Formoterol Fumarate Suspension

| Formulation | % w/w |
| --- | --- |
| FF | 0.009 |
| Bulking agent | 0.066 |
| Ethanol | 1.000 |
| HFA 227 | 98.925 |
| HFA 134.a | |
|  | 100.000 |

The bulking agent was selected from the following list, which also gives densities determined by Pycnometry.

| Sample | Density, g/ml |
| --- | --- |
| DL-Alanine | 1.3963 |
| Ascorbic acid | 1.6955 |
| Glucose (dextrose) | 1.5264 |
| Lactose, monohydrate | 1.5379 |
| D(+) Trehalose dihydrate | 1.5036 |

The Alanine bulked formulation formed flocs more slowly than either of the two Lactose bulked formulations which could improve dosing characteristics. The flocs were suspended in the vial, and appeared to be density matched at the laboratory temperature of 22° C.

All of the other bulking agents examined formed rapidly flocculating suspensions, which then sedimented.

EXAMPLES 26 to 28 to Alanine bulking agent with propellant mixtures.

The following formulations were prepared:

| | Example | | |
| --- | --- | --- | --- |
| | 26 | 27 | 28 |
| Propellant ratio (w/w) | 62.5% HFA 227 37.5% HFA 134a | 75% HFA 227 25% HFA 134a | 100% HFA 227 |
| % w/w | | | |
| FF | 0.10 | 0.10 | 0.009 |
| bulking agent | 0.069 | 0.068 | 0.066 |
| Ethanol | 1.000 | 1.000 | 1.000 |
| HFA 227 | 61.826 | 74.192 | 98.925 |
| HFA 134a | 37.095 | 24.731 | |
| | 100.000 | 100.000 | 100.000 |

Visual Assessment

The resultant suspensions were examined visually. As before, the Alanine suspensions formed smaller flocs, which formed more slowly than those of the Lactose bulked suspensions. At the laboratory temperature of 25° C., the suspensions in Example 28 appeared to rise towards the surface of the liquid, although a creamed layer was not observed.

Example 27 appeared to be density matched, with the flocs gradually settling to the bottom of the vial. Example 26 settled to the bottom of the vial more rapidly.

On standing overnight, Example 28 had creamed and formed a layer occupying approximately the top third of the liquid layer. In the two suspensions with lower HFA 227 ratios, the flocs had settled to the bottom of the vial.

Thus, the use of Alanine allows the preparation of formulations in which the density of the suspended solids is a close match to that of the liquid component. Furthermore, the volume of sedimented or creamed solids is found to be advantageously larger than for formulations without such a density match.

The slower flocculation rate of suspended Alanine permits higher levels of it to be used as a bulking agent without causing undesirably rapid flocculation of the drug formulation, for example in a ratio of 1:100 drug: Alanine.

EXAMPLES 29 to 33

The following formulations were prepared:

| | Example | | | | |
| --- | --- | --- | --- | --- | --- |
| | 29 % w/w | 30 % w/w | 31 % w/w | 32 % w/w | 33 % w/w |
| FF | 0.011 | 0.011 | 0.011 | 0.009 | 0.009 |
| Oleic acid | 0.000 | 0.000 | 0.010 | 0.000 | 0.000 |
| Ethanol | 1.000 | 2.000 | 2.499 | 1.000 | 2.000 |
| HFA 134a | 98.989 | 97.989 | 97.480 | | |
| HFA 227 | | | | 98.991 | 97.991 |
| | 100.000 | 100.000 | 100.000 | 100.000 | 100.000 |

The formulations of Examples 29 to 31 produced well dispersed, slowly flocculating suspensions which gradually sedimented. The presence of surfactant increased the floc size.

The formulations of Examples 32 and 33 produced well dispersed, slowly flocculating suspensions which gradually creamed.

We claim:

1. A pharmaceutical suspension formulation suitable for aerosol administration, consisting essentially of:
   (a) from 0.0025 to 0.1% w/w of micronized formoterol, or an acid addition salt thereof and
   (b) from 0.1 to 5.0% w/w ethanol,
   (c) HFA 134a, HFA 227 or a mixture of HFA 227 and HFA 134a and optionally
   (d) a surfactant other than a monoacetylated or diacetylated monoglyceride,
   the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug.

2. An aerosol formulation as claimed in claim 1 which comprises HFA 134a and HFA 227 in a weight ratio of HFA 134a:HFA 227 in the range 50:50 to 30:70.

3. An aerosol formulation as claimed in claim 2 in which the weight ratio of HFA 134a:HFA 227 is about 37.5:62.5.

4. An aerosol formulation as claimed in claim 1 which comprises about 1 to 5% w/w ethanol.

5. An aerosol formulation as claimed in claim 1 which comprises about 0.01% w/w formoterol fumarate.

6. An aerosol formulation as claimed in claim 1 which comprises oleic acid.

7. An aerosol formulation as claimed in claim 6 in which the oleic acid is present in an amount of from 0.002 to 0.010% w/w.

8. An aerosol formulation as claimed in claim 6 in which the oleic acid is present in an amount of about 0.005% w/w.

9. An aerosol composition as claimed in claim 1 consisting of:

| Formoterol fumarate | 0.010 |
| --- | --- |
| Ethanol | 2.500 |
| HFA 227 | 60.931 |
| HFA 134a | 36.559 |

10. An aerosol composition as claimed in claim 1 consisting of:

| | |
|---|---|
| Formoterol fumarate | 0.020 |
| Oleic Acid | 0.005 |
| Ethanol | 2.500 |
| HFA 227 | 60.928 |
| HFA 134a | 36.557 |

11. A pharmaceutical suspension formulation suitable for aerosol administration, consisting essentially of:
  (a) from 0.0025 to 0.1% w/w of micronized formoterol, or an acid addition salt thereof,
  (b) from 0.1 to 5.0% w/w ethanol,
  (c) a propellant consisting of HFA 134a, HFA 227 or a mixture of HFA 227 and HFA 134a,
  (d) a micronized bulking agent in a weight ratio in the range from 1:3 to 1:100 of Formoterol bulking agent, and optionally
  (e) a surfactant,
the formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug.

12. A pharmaceutical suspension formulation as claimed in claim 11 comprising about 1% ethanol.

13. A pharmaceutical suspension formulation as claimed in claim 11 in which said weight ratio of formoterol fumarate to bulking agent is in the range 1:4 to 1:20.

14. A pharmaceutical suspension formulation as claimed in claim 13 in which said weight ratio of formoterol fumarate to bulking agent is about 1:7.

15. A pharmaceutical suspension formulation as claimed in claim 11 in which the bulking agent is selected from lactose, DL-Alanine, ascorbic acid, glucose and D+ trehalose dehydrate.

16. A pharmaceutical suspension formulation as claimed in claim 15 in which the bulking agent is lactose or DL-Alanine.

17. A pharmaceutical suspension formulation as claimed in claim 11 in which the propellant is HFA 227.

18. A pharmaceutical suspension formulation as claimed in claim 11 consisting of:

| | |
|---|---|
| Formoterol fumarate | 0.132 |
| Lactose | 0.924 |
| Ethanol | 14.058 |
| HFA 227 | 1390.686 |

19. An aerosol dispensing device comprising a container equipped with a metered dose dispensing valve and containing an aerosol formulation as claimed in claim 1.

* * * * *

UNITED STATES PATENT AND TRADEMARK OFFICE
CERTIFICATE OF CORRECTION

PATENT NO. : 6,054,488
DATED : April 25, 2000
INVENTOR(S) : Martin J. Oliver, Simon G. Paling, Philip A. Jinks, and Sukhbinder K. Jaiswal It is certified that error appears in the above-identified patent and that said Letters Patent is hereby corrected as shown below:

Column 11,
Line 3, please change "Formoterol fumarate 0.020" to -- Formoterol fumarate 0.010 --.

Signed and Sealed this

Fifth Day of March, 2002

Attest:

Attesting Officer

JAMES E. ROGAN
*Director of the United States Patent and Trademark Office*